(12) United States Patent
Chang et al.

(10) Patent No.: US 9,643,181 B1
(45) Date of Patent: May 9, 2017

(54) INTEGRATED MICROFLUIDICS SYSTEM

(71) Applicant: International Business Machines Corporation, Armonk, NY (US)

(72) Inventors: Hung-Yang Chang, Scarsdale, NY (US); Ning Li, White Plains, NY (US); Fei Liu, Yorktown Heights, NY (US); Qiqing C. Ouyang, Yorktown Heights, NY (US); Seshadri Subbanna, Brewster, NY (US); Yajuan Wang, White Plains, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/017,998

(22) Filed: Feb. 8, 2016

(51) Int. Cl.
| | |
|---|---|
| *G01N 21/64* | (2006.01) |
| *B01L 3/00* | (2006.01) |
| *G01N 15/10* | (2006.01) |
| *G01N 15/14* | (2006.01) |

(52) U.S. Cl.
CPC ... *B01L 3/502715* (2013.01); *B01L 3/502707* (2013.01); *G01N 21/6486* (2013.01); *B01L 2200/10* (2013.01); *B01L 2200/12* (2013.01); *B01L 2300/0636* (2013.01); *B01L 2300/0887* (2013.01); *B01L 2300/12* (2013.01); *G01N 15/1056* (2013.01); *G01N 15/1484* (2013.01)

(58) Field of Classification Search
CPC ......... H01L 29/78696; H01L 21/02472; H01L 21/0254; H01L 2924/12041; F21Y 2101/02; B01L 2300/0636; B01L 2300/0627; G01N 15/1056; G01N 15/1484

USPC ............ 435/288.7; 438/29; 422/82.05, 68.1; 427/100

See application file for complete search history.

(56) References Cited

U.S. PATENT DOCUMENTS

| | | | |
|---|---|---|---|
| 6,100,541 A | 8/2000 | Nagle et al. | |
| 6,197,503 B1 | 3/2001 | Vo-Dinh et al. | |
| 6,448,064 B1 | 9/2002 | Vo-Dinh et al. | |
| 7,291,497 B2 | 11/2007 | Holmes et al. | |
| 7,319,046 B2 | 1/2008 | Misiakos et al. | |
| 8,097,926 B2 * | 1/2012 | De Graff ........... | H01L 27/14618 257/419 |
| 8,101,402 B2 | 1/2012 | Holmes | |
| 2008/0081332 A1 | 4/2008 | Amano | |
| 2011/0034912 A1 * | 2/2011 | de Graff ........... | H01L 27/14618 606/21 |
| 2011/0262307 A1 | 10/2011 | Packirisamy et al. | |
| 2011/0312753 A1 | 12/2011 | Azimi et al. | |
| 2014/0030799 A1 | 1/2014 | Yu et al. | |
| 2014/0073884 A1 | 3/2014 | Yu et al. | |

FOREIGN PATENT DOCUMENTS

CN  103667012 B  3/2015

* cited by examiner

*Primary Examiner* — Lyle Alexander
*Assistant Examiner* — Bryan Kilpatrick
(74) *Attorney, Agent, or Firm* — Scully, Scott, Murphy & Presser, P.C.; Louis J. Percello, Esq.

(57) ABSTRACT

A microfluidic system-on-a-chip includes signal processing, light generation and detection, and fluid handling functions formed on a single substrate. The disclosed integrated system has a smaller footprint than device structures where individual components are manufactured separately and then assembled. Moreover, the integrated system obviates alignment challenges associated with conventionally packaged architecture.

20 Claims, 3 Drawing Sheets

INTEGRATED MICROFLUIDICS SYSTEM

BACKGROUND

The present application relates generally to microfluidic devices, and more specifically to the integration of micro- or nanofluidics together with logic and sensing functions on a single substrate.

Microfluidic techniques have been developed for a wide variety of biological engineering applications, though most microfluidic systems exhibit limited functionality. A number of emerging platforms, including capillary driven microfluidics, centrifugal microfluidics, and multiphase microfluidics have the potential to expand the efficacy of microfluidics across a variety of biological engineering applications.

In an example application, microfluidic devices can be used for body fluid diagnostics, including disease detection and health monitoring. The monitoring of glucose levels, for example, can be used to regulate insulin intake. For such an application, the microfluidic devices are advantageously portable and wearable, and comprise a fully-integrated platform that includes, inter alia, fluid handling, sensing and logic capabilities.

Thus, there is a need for economical and robust manufacturing of microfluidic devices.

SUMMARY

A monolithically integrated microfluidic lab on a chip includes sample handling and imaging functions in addition to integrated logic and/or memory. An example microfluidic system includes a microfluidic channel, a light source, a light detector, and associated CMOS circuitry.

In accordance with embodiments of the present application, a microfluidic device includes a semiconductor substrate, a light source and a light detector on the semiconductor substrate, and a microfluidic flow channel within a dielectric layer disposed over the substrate.

A method of forming a microfluidic device includes forming a light source and a light detector on a semiconductor substrate, depositing a dielectric layer over the semiconductor substrate, the light source and the light detector, and forming a microfluidic flow channel within the dielectric layer.

BRIEF DESCRIPTION OF SEVERAL VIEWS OF THE DRAWINGS

The following detailed description of specific embodiments of the present application can be best understood when read in conjunction with the following drawings, where like structure is indicated with like reference numerals and in which.

DETAILED DESCRIPTION

Figure 1:
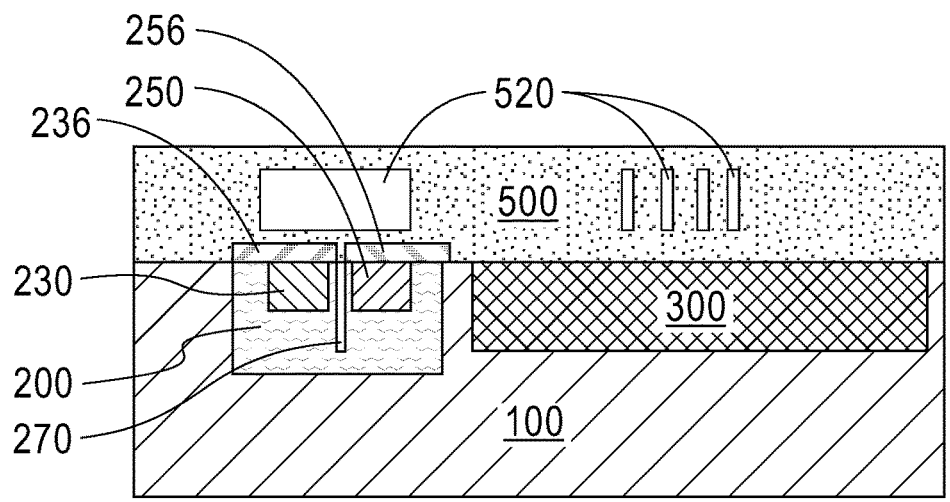
FIG. 1 is a schematic cross-sectional illustration of an integrated microfluidic device according to embodiments.

Reference will now be made in greater detail to various embodiments of the subject matter of the present application, some embodiments of which are illustrated in the accompanying drawings. The same reference numerals will be used throughout the drawings to refer to the same or similar parts.

An example integrated microfluidic device is shown schematically in FIG. 1. The device is formed on a single semiconductor substrate 100, and includes integrated circuitry 300, a light source 230, a photodetector 250, and microfluidic flow channels 520 formed in a dielectric layer 500 and located proximate to the LED 230 and photodetector 250.

Substrate 100 may comprise a semiconductor material such as silicon or a silicon-containing material, including a bulk substrate. Silicon-containing materials include, but are not limited to, single crystal Si, polycrystalline Si, single crystal silicon germanium (SiGe), polycrystalline silicon germanium, silicon doped with carbon (Si:C), amorphous Si, as well as combinations and multi-layers thereof. Example silicon substrates include silicon-on-insulator (SOI) substrates, silicon-on-sapphire (SOS) substrates, and the like. As used herein, the term "single crystal" denotes a crystalline solid, in which the crystal lattice of the entire sample is substantially continuous and substantially unbroken to the edges of the sample with substantially no grain boundaries.

Substrate 100 is not limited to silicon-containing materials, as the substrate 100 may comprise other semiconductor materials, including Ge and compound semiconductors such as GaAs, InAs and other like semiconductors.

The substrate 100 may have dimensions as typically used in the art. Example substrate diameters include, but are not limited to, 50, 100, 150, 200, 300 and 450 mm. The total substrate thickness may range from 250 microns to 1500 microns, though in particular embodiments the substrate thickness is in the range of 725 to 775 microns, which corresponds to thickness dimensions commonly used in silicon CMOS processing.

Referring now to FIGS. 2-6, illustrated is an example method for forming a microfluidic device (e.g., biosensor) having microfluidic channels, circuitry (e.g., logic and/or memory), and sensing functions (e.g., light source and detector) integrated on a single semiconductor substrate.

Figure 2:
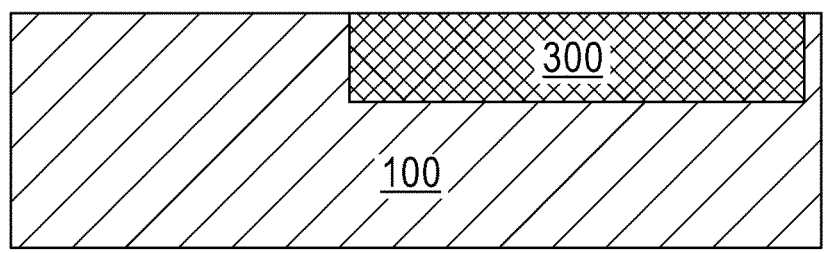
FIG. 2 shows the incorporation of various integrated circuits into a semiconductor substrate.

As shown schematically in FIG. 2, electronic circuitry 300 may be formed in substrate 100 using CMOS technology. In embodiments, circuitry 300 may be formed at processing temperatures of at most 1000° C. The electronic circuitry 300 can be made from a CMOS integrated circuit such as, for example 0.35 micron technology, 0.25 micron technology, or 0.18 micron technology, through smaller or larger technology nodes may be used. The CMOS architecture may include front end of the line structures comprising transistors, memory cell, electrical contacts, and the like. In embodiments, back end metallization using, for example, Al, W and/or Cu, is delayed until after the formation of various on-chip electronic devices as described in more detail below.

Figure 3:
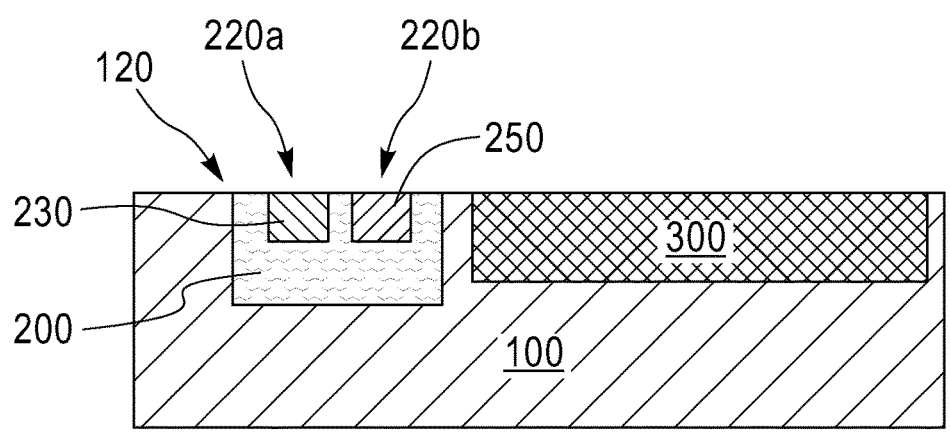
FIG. 3 shows the formation of a light emitting diode (LED) and photodetector on the semiconductor substrate of FIG. 2.

As depicted in FIG. 3, in a region of the substrate 100 separate from the electronic circuitry 300, a trench 120 may be formed using an isotropic or anisotropic etch of the substrate material. Anisotropic etching of silicon, for example, may be performed using tetramethylammonium hydroxide (TMAH), potassium hydroxide (KOH) or ethylenediamine pyrocatechol (EDP).

Electronic devices such as, for example, a light source 230 (e.g., laser diode (LD) or a light-emitting diode (LED) device) and/or a photodetector 250 (e.g., a PIN photodiode or an avalanche photodiode (APD)) may then be fabricated within trench 120 such that the electronic devices are co-integrated on a same substrate. In embodiments, electronic devices can be formed at processing temperatures of less than 650° C.

In the present embodiment, a light source 230 such as an LED can be formed within trench 120, i.e., below the top surface of substrate 100. In embodiments, light source 230 is adapted to produce one or more of ultraviolet (UV) light, infrared (IR) light or visible light. Light source 230 may be formed using an epitaxial gallium structure as known to those skilled in the art. For example, in performing the epitaxial growth process, a seed layer (not shown) may first be deposited over the substrate 100 within the trench 120. The seed layer may include, for example, aluminum nitride (AlN). In embodiments, a GaN material is then epitaxially grown on the seed layer to provide GaN layer 200. The epitaxial growth process for forming the GaN layer 200 may include, for example, MOCVD (metal organic chemical vapor deposition) or MBE (molecular beam epitaxy). In the present embodiment, the substrate 100 is a silicon substrate. In embodiments, the thickness of GaN layer 200 may range from 2 to 5 microns.

The terms "epitaxy," "epitaxial" and/or "epitaxial growth and/or deposition" refer to the growth of a semiconductor material layer on a deposition surface of a semiconductor material, in which the semiconductor material layer being grown assumes the same crystalline habit as the semiconductor material of the deposition surface. For example, in an epitaxial deposition process, chemical reactants provided by source gases are controlled and the system parameters are set so that depositing atoms alight on the deposition surface and remain sufficiently mobile via surface diffusion to orient themselves according to the crystalline orientation of the atoms of the deposition surface. Therefore, an epitaxial semiconductor material has the same crystalline characteristics as the deposition surface on which it is formed. For example, an epitaxial semiconductor material deposited on a (100) crystal surface will take on a (100) orientation.

Figure 4:
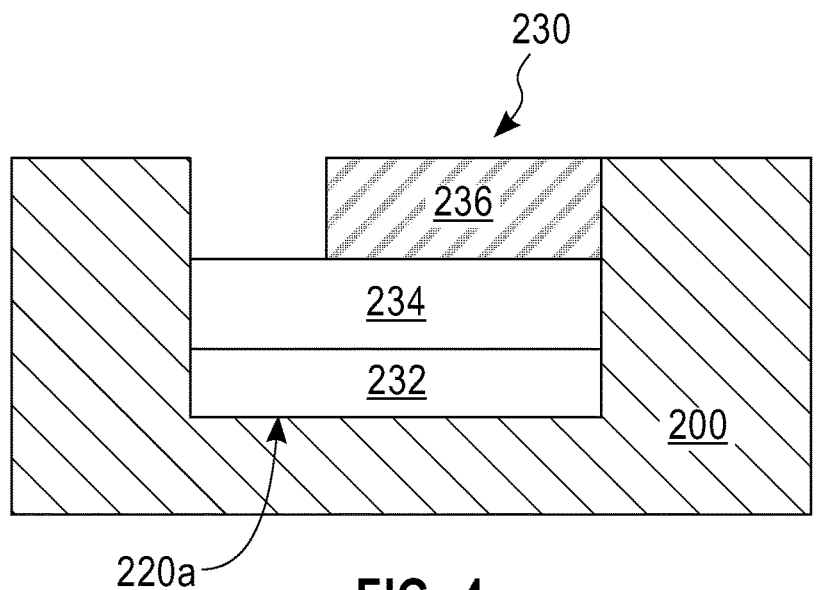
FIG. 4 is a cross-sectional view depicting the formation of doped GaN layers of first and second conductivity types to form an LED.

By way of example, the GaN layer 200 may be etched using, for example, one of a reactive ion etching (RIE) or a wet etching process to form trenches 220a, 220b. Referring to FIG. 4, an optional seed layer 232 such as, for example, AlN, is deposited on the exposed top surface of the gallium nitride layer 200 within trench 220a. A lower GaN layer 234 of a first conductivity type is then epitaxially grown on the seed layer 232 using, for example, MOCVD. The lower GaN layer 234 may be doped in-situ, or alternatively the lower GaN layer 234 may be doped subsequently to its formation using an ion implantation process or a gas phase doping process. In one embodiment, the lower GaN layer 234 is doped n-type with Si.

An upper GaN layer 236 of a second conductivity type that is opposite the first conductivity type is then epitaxially grown on the lower GaN layer 234 using, for example, MOCVD. The upper GaN layer 236 may be doped in-situ, or alternatively the upper GaN layer 236 may be doped subsequently using an ion implantation process or gas phase doping. In the illustrated embodiment, the upper GaN layer 236 is doped p-type with magnesium (Mg).

As used herein, "p-type" refers to the addition of impurities to an intrinsic semiconductor that creates a deficiency of valence electrons. For gallium nitride, an example p-type dopant, i.e., impurity, is magnesium. As used herein, "n-type" refers to the addition of impurities that contribute free electrons to an intrinsic semiconductor. For gallium nitride, example n-type dopants, i.e., impurities, include but are not limited to, carbon, silicon and germanium. The dopant(s) may be introduced by ion implantation or may be introduced, for example, in situ, i.e., during a process sequence used to form the layer. As an alternative to the configuration described above, the lower GaN layer 234 may contain a p-type dopant, while the upper GaN layer 236 contains an n-type dopant.

Then, using an etching mask such as a hard mask, a portion of the exposed portion of the upper GaN layer 236 is etched using, for example, an RIE etching process to expose a portion of the top surface of the lower GaN layer 234. The hard mask and/or photoresist are then removed from the upper GaN layer 236 using conventional methods known in the art. For instance, the photoresist can be removed by ashing, or can be consumed during the etch process that removes a portion of the upper GaN layer 236.

At this stage and after forming the light source 230, other electronic devices such as a photodetector 250 (or photodetector array) may be formed on the structure illustrated in FIG. 3. In an embodiment, the photodetector 250 may be formed of GaN within trench 220b (i.e., below the top surface of substrate 100) and integrated with the light source on the same wafer.

Figure 5:
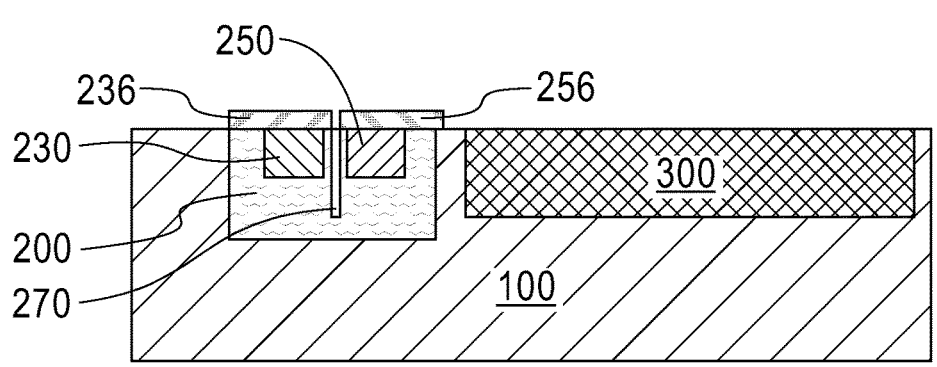
FIG. 5 depicts the formation of optical filters for the LED and photodetector of FIG. 3.

As shown in FIG. 5, a barrier layer 270 is formed within gallium nitride layer 200 between the light source 230 and the photodetector 250. In embodiments, the barrier layer 270 is configured as a light-blocking layer and prevents light emitted by the light source from passing through the gallium nitride layer 200 to the photodetector 250.

Barrier layer 270 may be formed by initially etching a trench into the gallium nitride layer between the light source 230 and the photodetector 250, and then coating at least the sidewalls of the trench with a light-blocking material of sufficient thickness to block the transmission of light therethrough. In embodiments, light transmission through the barrier layer is less than 5%, e.g., 2%, 1% or 0%. The light-blocking material may partially or completely fill the trench etched into the gallium nitride layer 200. Example light-blocking materials include metals such as copper, silver and aluminum, which may be deposited, for example by electroplating or CVD, to a thickness of 10 to 100 nm.

As also shown in FIG. 5, one or more spectral filters 236, 256 may be incorporated into the device architecture. For example, light source 230 may be provided with a first spectral filter 236. The first spectral filter 236 is operable to transmit a first set of spectral bands and block a second set of spectral bands from the light source 230. The first spectral filter 236 may be based on retarder stack technology or dichromic filter technology.

In a similar vein, photodiode 250 may be provided with a second spectral filter 256. Second spectral filter 356 is configured to pass light with a predetermined optical bandwidth. In embodiments, first and second spectral filters 236, 256 are formed over the light source 230 and photodetector 250 structures, respectively.

Figure 6:
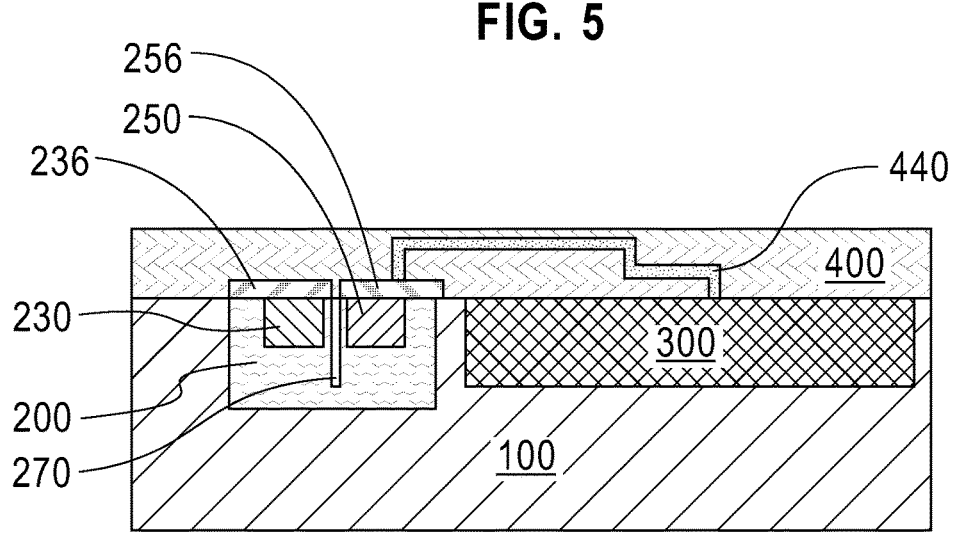
FIG. 6 illustrates a device architecture after the formation of an interconnect structure.

Referring now to FIG. 6, and after forming the electronic devices (e.g., light source 230 and photodetector 250), a dielectric layer 400 is formed over a top surface of the substrate using, for example, a CVD process. Dielectric layer 400 may comprise silicon dioxide. In embodiments, the thickness of dielectric layer 400 may range from 0.2 to 5 microns.

Using photolithography and etching methods known to those skilled in the art, electrical contacts 440 can be formed within dielectric layer 400, for example, to provide electrical contact between one or more of the light source 230, photodetector 250 and circuitry 300. Photolithography steps may include priming, photoresist spin-coating, soft-bake, exposure, development, etc. According to embodiments, apertures may be provided, e.g., etched through dielectric layer 400 to expose metal bond pads of electronic circuitry previously-formed in the substrate 100, and then filled with a suitable material to form contacts 440. Apertures may be formed by any suitable method, such as using lithography and dry and/or wet etching, for example deep reactive ion etching (DRIE). Contacts 440 may comprise a metal or a metal alloy and may be formed by any chemical or physical vapor deposition method, such as CVD, electron-beam evaporation, filament evaporation, or sputter deposition.

Figure 7:
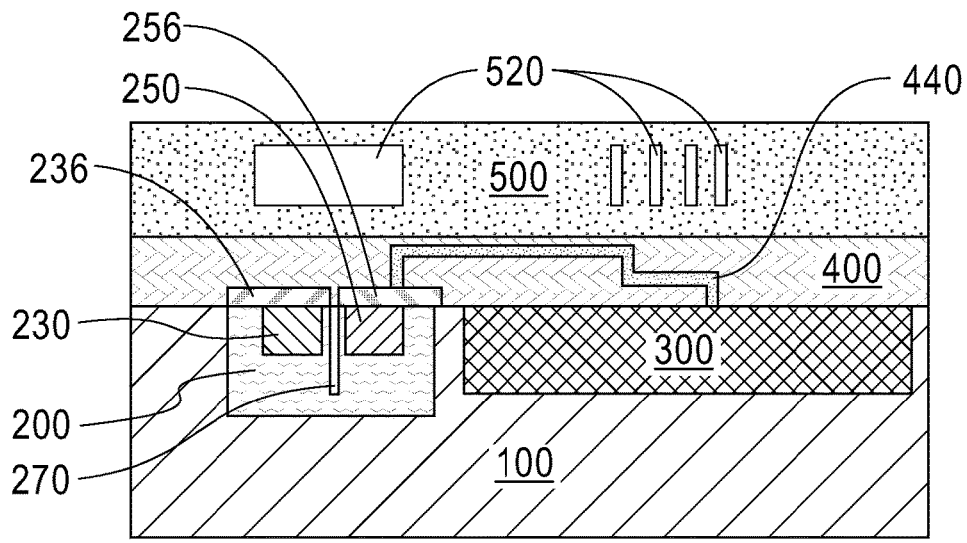
FIG. 7 shows the formation of microfluidic channels over the interconnect structure of FIG. 6.

Referring to FIG. 7, a further dielectric layer 500 is formed over dielectric layer 400 using, for example, a CVD process. Dielectric layer 500 may comprise silicon dioxide and may have a layer thickness of, for example, 1 to 10 microns. A portion of the dielectric layer 500 can be patterned using a layer of photoresist and optionally a hard mask (not shown) and then etched using a reactive ion etch or a wet etch to form microfluidic channels 520 in the dielectric layer 500.

In a further embodiment, microfluidic channels 520 may be formed using a selective etching process. This technique includes the deposition and definition of a sacrificial layer (not shown) on the dielectric layer 500, deposition of additional dielectric material to encapsulate the patterned sacrificial layer, and then an anisotropic etch to remove the sacrificial layer, to form microfluidic channels 520. In embodiments where the dielectric layer 500 comprises silicon dioxide, the sacrificial layer may comprise silicon, which may be selectively removed using, for example, a xenon difluoride-based etch.

The microfluidic channels 520 may comprise buried channels, which are formed within a single layer of material, as opposed to a channels that are made by joining together two substrates that include a channel or two half channels formed therein. Example microfluidic channels 520 may be characterized by a length dimension (i.e., length, width, or depth) of 10 to 500 μm.

As illustrated with respect to FIGS. 2-6, disposed over semiconductor substrate 100 is a microfluidic system that includes logic and/or memory circuitry 300, a light source 230, a photodetector 250, and microfluidic channel 520. During use, the microfluidic channels 520 can contain analytes to be analyzed therein as will be discussed in more detail hereinafter.

In embodiments, at least one microfluidic channel 520 is operatively connected to the light source 230 and to the photodetector 250 such that light emitted from the light source 230 enters into the microfluidic channel 520, while both excited light (e.g., light emitted from the light source 230 that is absorbed and excited by particles attached to an analyte flowing in the microfluidic channel 520) and un-excited light (e.g., light emitted from the light source 230 that is not absorbed by the particles attached to the analyte flowing the microfluidic channel 520 and that remains un-attenuated) exiting the microfluidic channel 520 can enter the photodetector 250. The photodetector 250 converts the received excited light into an electrical signal for analysis, which may be performed by circuitry 300.

In some embodiments, the disclosed system is a biosensor chip that may be used to analyze biological analytes, although embodiments are not limited thereto. During operation, particles (e.g., fluorescent particles) are attached to an analyte (not shown) of interest, such as deoxyribonucleic acid (DNA), ribonucleic acid (RNA), proteins, viruses, etc., using conventional techniques known in the art. The particles that are attached to the analyte emit fluorescent light in the UV range when excited by UV excitation light. Alternatively, and in other embodiments, the particles attached to the analyte may emit IR or visible light.

The analyte and particles attached thereto flow in the microfluidic channel 520 using conventional techniques and materials. The light source 330 emits an excitation light (e.g., UV light), which enters into microfluidic channel 520. In the microfluidic channel 520, some of the excitation light is absorbed by the particles attached to the analyte to emit fluorescent UV light having a different wavelength than the excitation light, while some of the excitation light does not get absorbed by any of particles.

Excitation light absorbed by the particles is emitted by the particles as fluorescent UV light having a different wavelength than the excitation light in several different directions such that some of the emitted fluorescent UV light is emitted into the photodetector 250 while some of the emitted fluorescent light travels into other areas of the microfluidic channel 520.

The effect of the excitation light reaching the photodetector 250 may be minimized through the use of optical filters 256, which prevent the passage of the excitation light not absorbed by particles into the photodetector 250.

Figure 8:
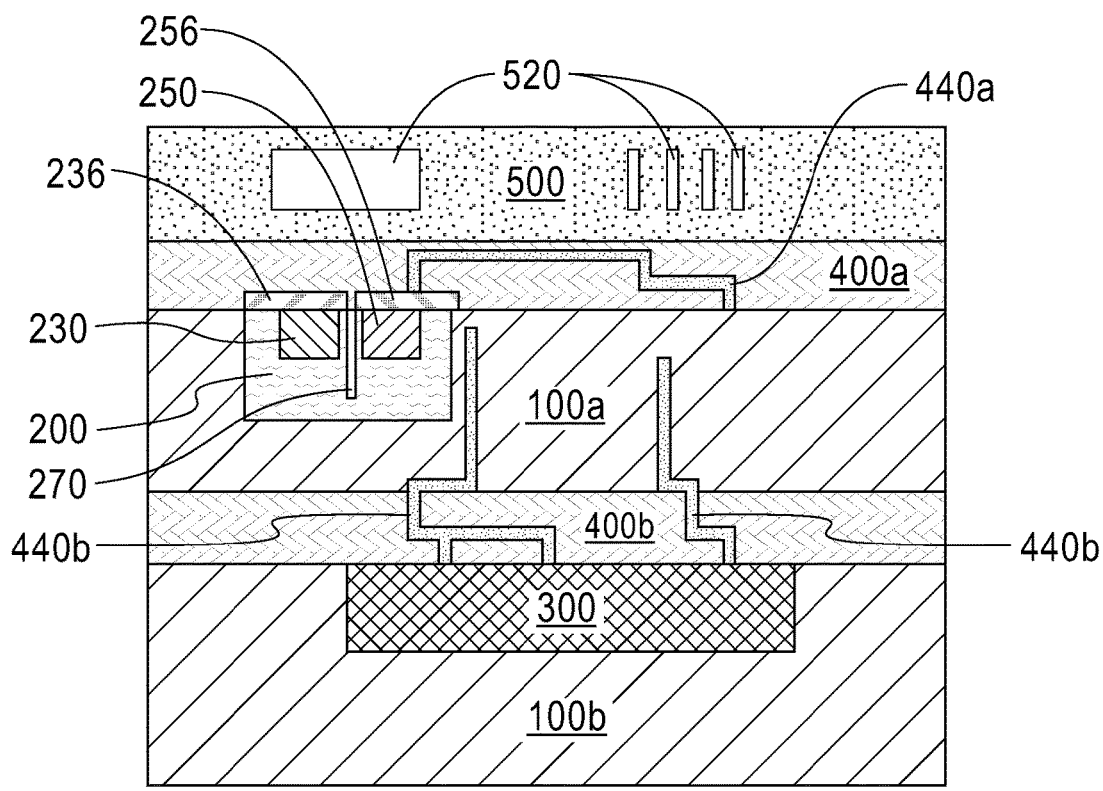
FIG. 8 is an example integrated microfluidic device according to further embodiments.

A microfluidic system according to a further embodiment is illustrated schematically in FIG. 8. A light source 230 and a photodetector 250 are formed in a first semiconductor substrate 100a as described above. As in the previous embodiment, a dielectric layer 400a having electrical contacts 440a formed therein is disposed over the substrate 100a, and a further dielectric layer 500 comprising microfluidic channels 520 is disposed over the dielectric layer 400a.

Electronic circuitry 300 is formed in a second semiconductor substrate 100b. In embodiments second semiconductor substrate 100b may be a silicon substrate, while first semiconductor substrate may be a silicon substrate or a III-V substrate. A dielectric layer 400b having electrical contacts 440b formed therein is disposed over the second substrate 100b. Further electrical contacts extending through substrate 100a may be used to form connections between electronic circuitry 300, light source 230 and photodetector 250 via conductive plugs 640 formed in optional interfacial layer 600. Interfacial layer 600 may be an interposer layer and may comprise silicon or a dielectric material such as silicon dioxide or a polymer material. Conductive plugs 640 may comprises through silicon vias.

Disclosed in various embodiments is a microfluidic system-on-a-chip having an vertically-integrated platform where signal processing, light generation and detection, and fluid handling functions are formed, i.e., successively formed, in a single substrate. The disclosed integrated manufacturing approach obviates alignment challenges incumbent to the separate manufacture and packing of discrete components and enables the production of a device having a smaller footprint than a conventionally-assembled structure.

As used herein, the singular forms "a," "an" and "the" include plural referents unless the context clearly dictates otherwise. Thus, for example, reference to a "light emitting diode" includes examples having two or more such "light emitting diodes" unless the context clearly indicates otherwise.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred. Any recited single or multiple feature or aspect in any one claim can be combined or permuted with any other recited feature or aspect in any other claim or claims.

It will be understood that when an element such as a layer, region or substrate is referred to as being formed on, deposited on, or disposed "on" or "over" another element, it can be directly on the other element or intervening elements may also be present. In contrast, when an element is referred to as being "directly on" or "directly over" another element, no intervening elements are present.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a dielectric layer that comprises a microfluidic channel include embodiments where a dielectric layer consists essentially of microfluidic channel and embodiments where a dielectric layer consists of a microfluidic channel.

It will be apparent to those skilled in the art that various modifications and variations can be made to the present invention without departing from the spirit and scope of the invention. Since modifications, combinations, sub-combinations and variations of the disclosed embodiments incorporating the spirit and substance of the invention may occur to persons skilled in the art, the invention should be construed to include everything within the scope of the appended claims and their equivalents.

What is claimed as new is:

1. A microfluidic device comprising:
   an integrated circuitry located in a first region of a semiconductor substrate;
   a trench located in a second region of the semiconductor substrate and filled with an epitaxial layer;
   a light source located in a first region of the epitaxial layer
   a light detector located in a second region of the epitaxial layer; and
   a microfluidic flow channel within a dielectric layer disposed over the semiconductor substrate and the epitaxial layer.

2. The microfluidic device of claim 1, wherein the integrated circuitry comprises transistors, memory cells and electrical contacts.

3. The microfluidic device of claim 1, wherein a top surface of each of the light source and the light detector is coplanar with a top surface of the semiconductor substrate.

4. The microfluidic device of claim 1, wherein the microfluidic flow channel is disposed over the light source and the light detector.

5. The microfluidic device of claim 1, further comprising an interconnect layer between the dielectric layer and the semiconductor substrate.

6. The microfluidic device of claim 1, wherein the epitaxial layer comprises gallium nitride.

7. The microfluidic device of claim 1, further comprising a light blocking layer within the epitaxial layer between the light source and the light detector.

8. The microfluidic device of claim 1, wherein the semiconductor substrate comprises silicon and the dielectric layer comprises silicon dioxide.

9. A method of forming a microfluidic device, comprising:
   forming an integrated circuitry in a first region of a semiconductor substrate;
   forming a first trench in a second region of the semiconductor substrate;
   filling the first trench with an epitaxial layer;
   forming a light source within a second trench formed in a first region of the epitaxial layer;
   forming a light detector within a third trench located in a second region of the epitaxial layer;
   depositing a dielectric layer over the semiconductor substrate, the dielectric layer covering the light source and the light detector; and
   forming a microfluidic flow channel within the dielectric layer.

10. The method of claim 9, further comprising forming an interconnect layer between the dielectric layer and the semiconductor substrate.

11. The method of claim 9, further comprising forming a light blocking layer within the epitaxial layer between the light source and the light detector.

12. The method of claim 9, wherein the light source is formed by epitaxially growing a lower gallium nitride layer of a first conductivity type and an upper gallium nitride layer of a second conductivity type that is opposite the first conductivity type within the second trench.

13. The method of claim 9, wherein the forming the microfluidic channel comprises etching a sacrificial layer formed on the dielectric layer.

14. The method of claim 12, further comprising forming a seed layer on a bottom surface of the second trench prior to the epitaxially growing the lower gallium nitride layer.

15. The method of claim 14, wherein the seed layer comprises aluminum nitride (AlN).

16. The method of claim 11, wherein the light blocking layer comprises copper, silver or aluminum.

17. The method of claim 11, wherein the forming the light blocking layer comprises:
   forming a trench into the epitaxial layer, wherein the trench is located between the light source and the light detector; and
   coating at least sidewalls of the trench with a light-blocking material.

18. The microfluidic device of claim 1, further comprising a first spectral filter located over the light source, and a second spectral filter located over the light detector, wherein the first spectral filter and the second spectral filter are laterally surrounded by the dielectric layer.

19. A microfluidic device comprising:
   an integrated circuitry located in a semiconductor substrate;
   a light source located in a first region of an epitaxial layer that is disposed over the semiconductor substrate;
   a light detector located in a second region of the epitaxial layer; and a microfluidic flow channel located within a dielectric layer that is disposed over the semiconductor substrate.

20. The microfluidic device of claim 19, further comprising a first interconnect layer located between the epitaxial layer and the semiconductor substrate, and a second interconnect layer located between the epitaxial layer and the semiconductor substrate.

* * * * *